US009603655B2

(12) United States Patent
Lutze et al.

(10) Patent No.: US 9,603,655 B2
(45) Date of Patent: Mar. 28, 2017

(54) ELECTROSURGICAL INSTRUMENT

(75) Inventors: Theodor Lutze, Balgheim (DE); Anton Keller, Dürbheim (DE); Dieter Weisshaupt, Immendingen (DE); Stefan Eick, Tuttlingen (DE); Christoph Rothweiler, Donaueschingen (DE); Eugen Herner, Villingen-Schwenningen (DE)

(73) Assignee: Aesculap AG (DE)

( * ) Notice: Subject to any disclaimer, the term of this patent is extended or adjusted under 35 U.S.C. 154(b) by 304 days.

(21) Appl. No.: 14/342,831

(22) PCT Filed: Sep. 14, 2012

(86) PCT No.: PCT/EP2012/068158
§ 371 (c)(1),
(2), (4) Date: Jun. 24, 2014

(87) PCT Pub. No.: WO2013/037975
PCT Pub. Date: Mar. 21, 2013

(65) Prior Publication Data
US 2014/0309635 A1 Oct. 16, 2014

(30) Foreign Application Priority Data
Sep. 16, 2011 (DE) .................. 10 2011 053 682

(51) Int. Cl.
A61B 18/14 (2006.01)
A61B 18/00 (2006.01)

(52) U.S. Cl.
CPC ...... A61B 18/1445 (2013.01); A61B 18/1482 (2013.01); A61B 2018/0063 (2013.01);
(Continued)

(58) Field of Classification Search
CPC ............ A61B 18/1452; A61B 18/1455; A61B 2018/1455; A61B 2018/1452; A61B 18/1442; A61B 18/1445
See application file for complete search history.

(56) References Cited

U.S. PATENT DOCUMENTS

| 5,891,142 A | 4/1999 | Eggers | |
| 2003/0014053 A1* | 1/2003 | Nguyen | A61B 18/1445 606/51 |

(Continued)

FOREIGN PATENT DOCUMENTS

| CN | 100544681 | 9/2009 |
| CN | 101522127 | 9/2009 |

(Continued)

OTHER PUBLICATIONS

Chinese Office Action dated Oct. 29, 2015 for Chinese Application No. 201280045066.1 with translation.

(Continued)

Primary Examiner — Jaymi Della
(74) Attorney, Agent, or Firm — RatnerPrestia

(57) ABSTRACT

An electrosurgical instrument includes a proximal end and a distal end having a jaw member assembly at the distal end including a first jaw member and a second jaw member movable relative thereto. The jaw members can be transferred relative to each other from an opening position into a gripping position in which they are arranged to be closer to each other than in the opening position. Each jaw member has at least one electrode connectable to an electric power source and electrodes of both jaw members being adapted to interact for sealing body tissue held between the jaw members in the gripping position, actuating means for transferring the jaw members from the opening position into the gripping position and means for limiting the closing width of (Continued)

Figure 1:
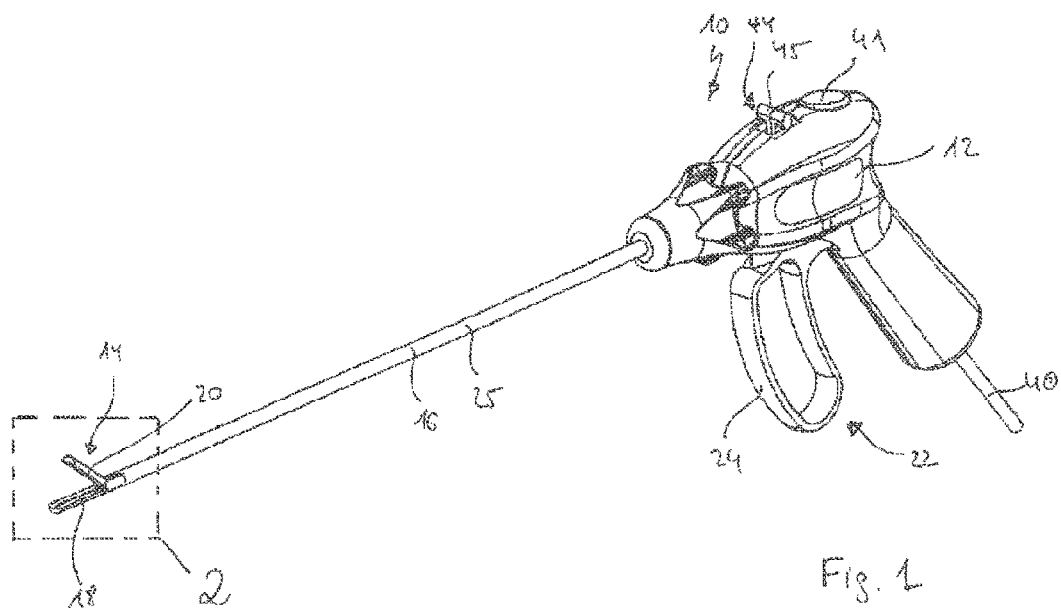

the jaw members, when they are transferred from the opening position into the gripping position.

8 Claims, 11 Drawing Sheets

(52) U.S. Cl.
CPC ............... *A61B 2018/00601* (2013.01); *A61B 2018/1455* (2013.01); *A61B 2018/1467* (2013.01)

(56) References Cited

U.S. PATENT DOCUMENTS

| | | | |
|---|---|---|---|
| 2004/0122423 A1* | 6/2004 | Dycus | A61B 18/1445 606/51 |
| 2004/0162557 A1 | 8/2004 | Tetzlaff et al. | |
| 2004/0249374 A1 | 12/2004 | Tetzlaff | |
| 2005/0107784 A1* | 5/2005 | Moses | A61B 17/285 606/51 |
| 2006/0271038 A1* | 11/2006 | Johnson | A61B 17/07207 606/45 |
| 2008/0045944 A1 | 2/2008 | Fischer | |
| 2010/0016857 A1 | 1/2010 | McKenna | |
| 2010/0057084 A1 | 3/2010 | Hanna | |
| 2010/0204698 A1 | 8/2010 | Chapman | |
| 2011/0082494 A1* | 4/2011 | Kerr | A61B 17/295 606/205 |
| 2011/0184404 A1 | 7/2011 | Walberg | |
| 2012/0083784 A1* | 4/2012 | Davison | A61B 18/1445 606/48 |
| 2012/0150167 A1 | 6/2012 | Fischer | |
| 2012/0271346 A1* | 10/2012 | Townsend | A61B 18/1445 606/205 |
| 2013/0274741 A1 | 10/2013 | Marczyk | |
| 2016/0157930 A1 | 6/2016 | Heard | |

FOREIGN PATENT DOCUMENTS

| | | |
|---|---|---|
| DE | 69925854 T2 | 5/2006 |
| DE | 102007053359 B3 | 6/2009 |
| DE | 102008018614 A1 | 10/2009 |
| DE | 102009037614 A1 | 2/2011 |
| EP | 1 123 058 B1 | 12/2005 |
| EP | 1 372 507 B1 | 6/2006 |
| JP | 2000102545 | 4/2000 |
| JP | 2002528167 | 9/2002 |
| JP | 2004524923 | 8/2004 |
| JP | 2004532676 | 10/2004 |
| JP | 2006006942 | 1/2006 |
| JP | 2006528909 | 12/2006 |
| JP | 2007319683 | 12/2007 |
| JP | 2010042248 | 2/2010 |
| JP | 2010051802 | 3/2010 |
| JP | 2010253278 | 11/2010 |
| WO | 0024331 | 5/2000 |
| WO | 02080796 | 10/2002 |
| WO | 02080797 | 10/2002 |
| WO | WO 02/080796 | 10/2002 |
| WO | 2004103156 | 12/2004 |
| WO | 2011018153 | 2/2011 |
| WO | 2011097469 | 8/2011 |

OTHER PUBLICATIONS

German Search Report issued in related German Application No. 10 2011 053 682.5, dated May 18, 2012.
International Search Report issued in related International Application No. PCT/EP/2012/068158, dated Nov. 26, 2012.
Japanese Office Action dated Aug. 24, 2016 for Japanese Application No. 2014-530246, including English translation, 9 pages.
Japanese Office Action for Japanese Application No. 2014-556987, dated Dec. 13, 2016 with translation, 5 pages.

* cited by examiner

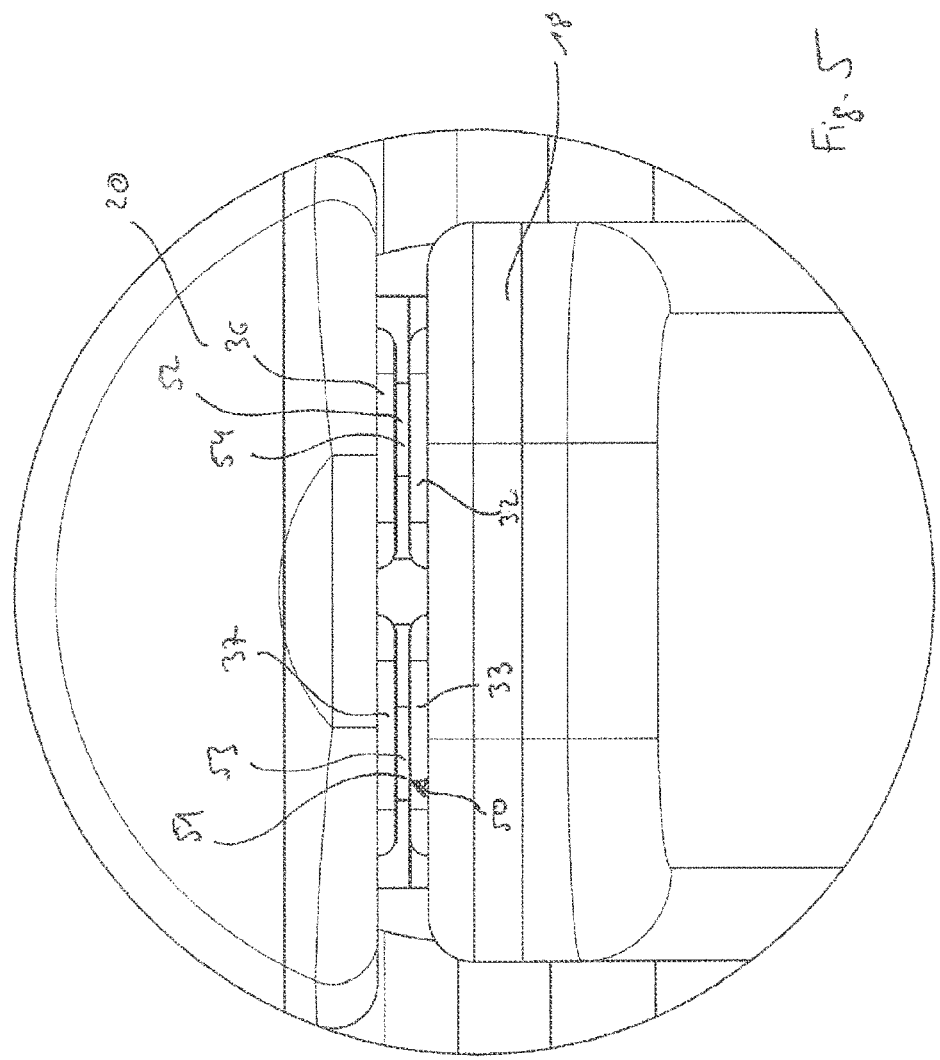

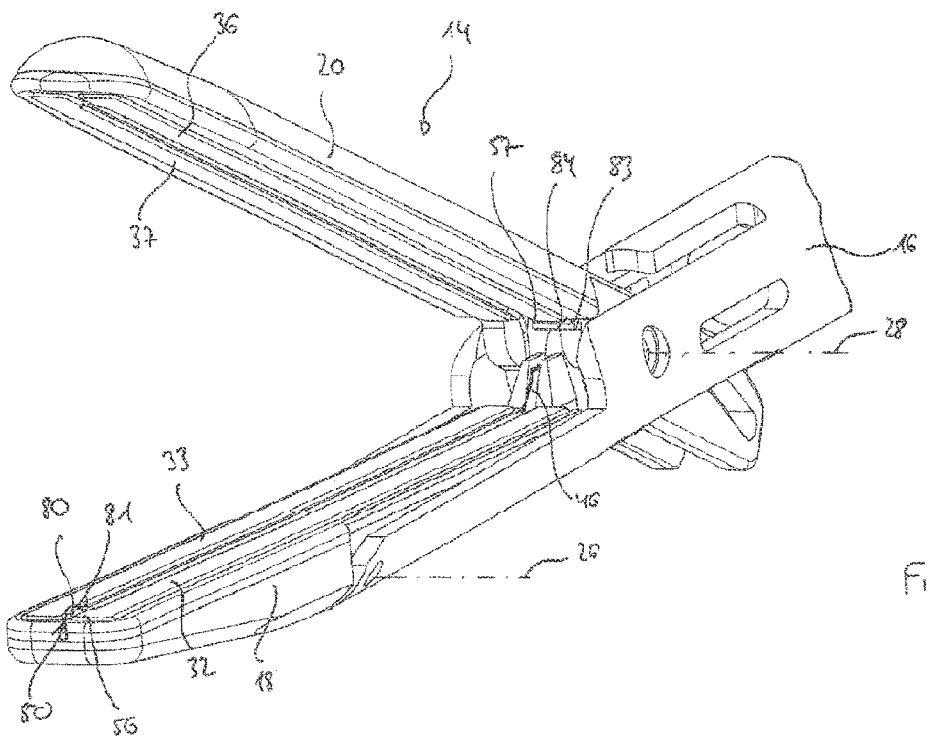
Fig. 16
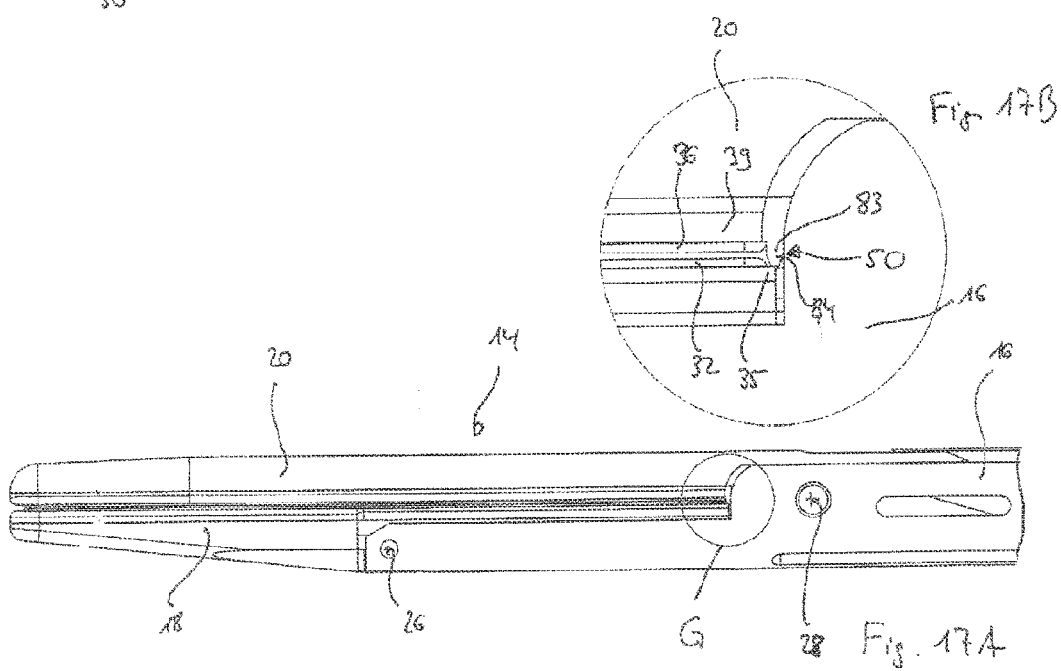
Fig. 17B
Fig. 17A

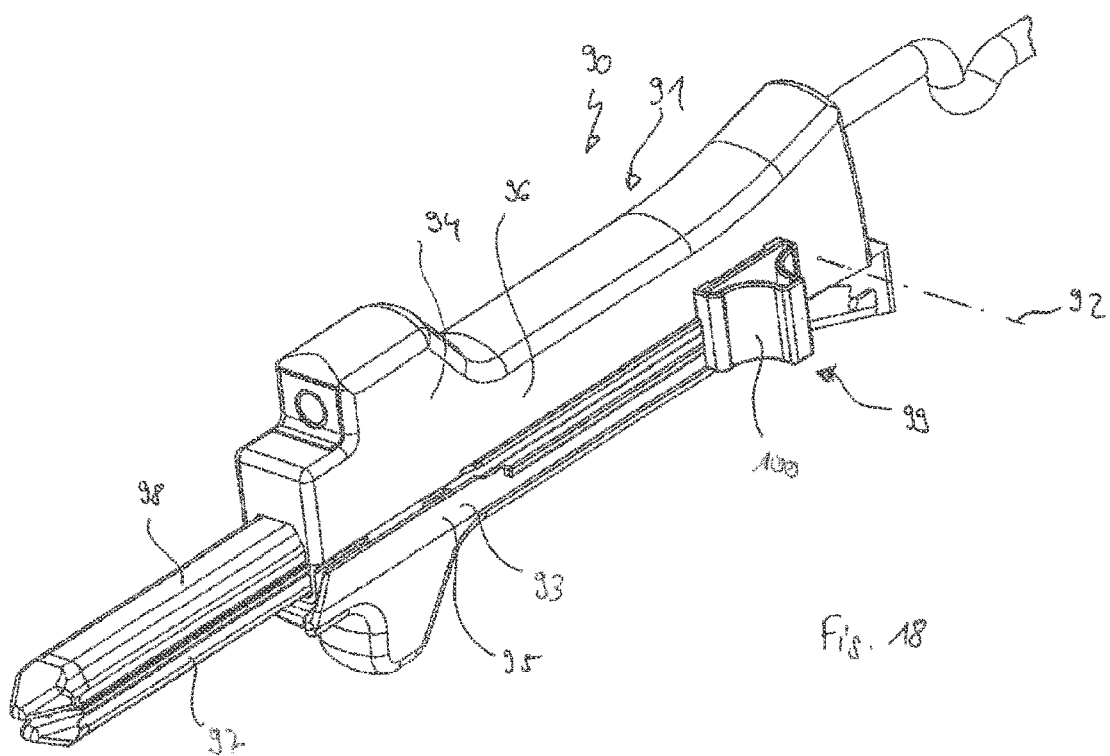

ELECTROSURGICAL INSTRUMENT

RELATED APPLICATIONS

This application is the U.S. national phase of International Application No. PCT/EP2012/068158, filed Sep. 14, 2012, which claims the benefit of priority of German Application No. 10 2011 053 682.5, filed Sep. 16, 2011, the contents of both applications being incorporated by reference herein in their entireties and for all purposes.

FIELD

The invention relates to an electrosurgical instrument including a proximal end and a distal end, comprising a jaw member assembly at the distal end which includes a first jaw member and a second jaw member movable relative to the former, the jaw members being adapted to be transferred relative to each other from an opening position into a gripping position in which gripping position they are arranged more closely to each other than in the opening position, wherein each jaw member has at least one electrode connectable to an electric power source and electrodes of both jaw members are adapted to interact for sealing body tissue held between the jaw members in the gripping position, actuating means for transferring the jaw members from the opening position into the gripping position and means for limiting the closing width of the jaw members, when they are transferred from the opening position into the gripping position.

BACKGROUND

An electrosurgical instrument is described, for example, in EP 1 123 058 B1 and in EP 1 372 507 B1. In order to seal body tissue by means of the instrument the jaw members can be transferred from the opening position into the gripping position via the actuating means so that tissue to be sealed is caught between the jaw members.

SUMMARY

In the present case the gripping position can also be referred to as closing position. By additionally applying electric voltage between the electrodes of both jaw members the body tissue can be sealed by electrosurgery. The means for limiting the closing width, hereinafter simply abbreviated to "means", is provided so that the jaw members are not approximated to each other so closely in the gripping position that the at least one electrode of the first jaw member and the at least one electrode of the second jaw member contact each other. In this way electric short-circuit is to be prevented between the electrodes of the jaw members.

The terms "proximal" and "distal" in the present case have to be understood to relate to a user manipulating the instrument. The user manipulates the instrument from the proximal end and acts on the body tissue by the distal end.

It is the object of the present invention to provide an electrosurgical instrument of the type mentioned in the beginning by which an improved sealing result can be achieved.

This object is achieved, according to the invention, in a generic electrosurgical instrument in that the means includes a plurality of limiting elements at most two limiting elements of which are disposed at one jaw member which limiting elements are configured as an electrically insulating spacer projecting from the jaw member toward the other jaw member over a sealing surface formed by the at least one electrode of the jaw member, at least one spacer thereof being arranged at a distal end portion of the jaw member assembly.

The means for limiting the closing width comprises a plurality of limiting elements. The limiting elements can be in the form of spacers with at least one spacer being provided. The spacer projects from the sealing surface of the at least one electrode of the jaw member to which it is fixed in the direction of the other jaw member and is capable of contacting the other jaw member. By means of the at least one spacer the electrodes can be largely prevented from contacting each other in the gripping position so that also short-circuit can be largely prevented. At least one spacer is disposed at a distal end portion, especially at the distal end of the jaw member assembly. In this way the closing width of the jaw members can be limited at the distal end portion which is especially advantageous in practice when the jaw members are formed to be curved toward each other at the distal end or are biased relative to each other. Furthermore, at one jaw member a total of at most two spacers are provided, wherein at each of the jaw members 0, 1 or 2 spacers can be provided. In practice, this turns out to be sufficient for preventing short-circuit of the electrodes in the gripping position, on the one hand, and to be beneficial to perfect sealing of the body tissue, on the other hand, because the number of spacers is limited to an as low number as possible. As a result, an improved sealing effect is obtained by means of the instrument according to the invention.

In an advantageous embodiment of the instrument according to the invention it turns out to be favorable, when only a total of two limiting elements in the form of spacers are provided. At least one of them is arranged, as explained before, at a distal end portion of the jaw member assembly.

The two spacers can be arranged, for example, at different jaw members so that one spacer is arranged at each jaw member.

It is also imaginable that the two spacers are arranged at the same jaw member and at the respective other jaw member no spacer is arranged.

In a different advantageous embodiment it may be provided that at each jaw member at least one spacer is arranged with at least one spacer thereof being disposed at a distal end portion of the jaw member assembly.

Furthermore, it may be provided that two spacers arranged at a jaw member are arranged in the proximal-distal direction at the same or substantially at the same position, wherein the two spacers can be arranged, for example, transversely to the proximal-distal direction laterally adjacent each other at the jaw member. This permits, for instance, to avoid transverse strain between the jaw members in the gripping position, especially when the spacers are disposed in symmetry relative to each other transversely to the proximal-distal direction at the jaw member. Thus the body tissue can be better caught.

It can be provided that at least two spacers, and especially all spacers, have an identical configuration.

In another advantageous embodiment of the instrument according to the invention, it can be provided that at the distal end portion of the jaw member assembly exactly one spacer is arranged.

For example, the spacer is arranged in the center of the distal end portion with respect to a direction orientated transversely to the proximal-distal direction.

Moreover, it is favorably provided that at least one or else exactly one spacer is arranged proximally relative to the distal end portion and especially at a proximal end portion of the jaw member. A limitation of the closing width thus can obtained also proximally, for instance at the proximal end portion of the jaw member and, consequently, electric short-circuit can be prevented.

Preferably, it can be provided that at least one spacer is integrated in the at least one electrode of the jaw member at which it is disposed. The electrode can comprise a recess in which the spacer is inserted, for instance. The electrode also can have a breakthrough through which the spacer passes the electrode in the direction of the respective other jaw member.

In particular, all spacers can be integrated in the at least one electrode of the jaw member to which they are fixed.

It is also favorable when at least one spacer is formed integrally with a support element of the jaw member at which it is disposed for the at least one electrode of said jaw member. This permits achieving a structurally simple configuration of the instrument.

In particular, all spacers can be formed integrally with a support element of the jaw member at which each of them is disposed for the at least one electrode of said jaw member.

It is beneficial when the instrument comprises a cutting means for severing body tissue held between the jaw members in the gripping position thereof, the cutting means including a cutting element which is or can be arranged transversely to the proximal-distal direction between two sealing surface portions of the respective at least one electrode of the jaw members. By means of such instrument the tissue cannot only be sealed but can also be severed by the cutting element. At each jaw member two sealing surface portions are provided transversely to the proximal-distal direction so that the body tissue can be sealed on both sides of the cutting element.

In an advantageous embodiment of the instrument the cutting element can be provided to be held at either of the jaw members.

In a different advantageous embodiment of the instrument the cutting means comprises an actuating element for moving the cutting element in the proximal-distal direction and for transferring the same from a retracted position into an advanced position, wherein body tissue held between the jaw members in the gripping position thereof during transfer is severed. This enables a user to activate the cutting function of the instrument only as required by acting on the actuating element.

It is imaginable that at least one jaw member has two separate electrodes each of which forms a sealing surface portion.

Furthermore, it is possible that at least one jaw member has an electrode forming both sealing surface portions.

In practice it turns out to be advantageous for uniformly limiting the closing width, when at least one spacer is arranged on each side of the cutting element transversely to the proximal-distal direction. In the case of the afore-mentioned movable cutting element this has to be understood as being related to a position thereof which it can adopt during transfer from the retracted position into the advanced position for severing tissue between the sealing surface portions.

It can especially be provided that exactly one spacer is arranged on each side of the cutting element.

It turns out to be favorable when the means for limiting the closing width comprises at least one further limiting element which is not in the form of a spacer and which is arranged proximally with respect to the at least one spacer disposed at the distal end portion of the jaw member assembly. This enables the closing width of the jaw members to be limited in an even more reliable manner, namely on the one hand by means of the at least one spacer at the distal end portion and, on the other hand, by means of another more proximal limiting element.

It is of advantage when the instrument includes a jaw member support for the first jaw member with the second jaw member being pivotal relative thereto for transferring the jaw members from the opening position into the gripping position, and when the first jaw member is pivotal relative to the jaw member support about a pivot axis orientated transversely to a longitudinal direction defined by said jaw member support. This is advantageous as upon transferring the jaw members into the gripping position the electrodes thereof can approximate to each other in parallel so that the jaw members can have a uniform distance over the entire sealing surfaces of the electrodes ideally in the proximal-distal direction and transversely thereto. The body tissue in this way can be sealed in a uniform and reliable manner.

It may be provided that the distal end of the first jaw member is biased in the direction of the distal end of the second jaw member so as to engage behind tissue to be sealed and thus better seize the same.

It is favorable when the means for limiting the closing width comprises at least one further limiting element in the form of a first stop member being arranged at the first jaw member as well as at least one further limiting element in the form of a second stop member being arranged at the jaw member support and interacting for limiting the pivoting motion of the first jaw member relative to the jaw member support such that the proximal end of the first jaw member is pivoted toward the second jaw member. The closing width of the jaw members can be limited even more reliably by the further limiting elements in the form of stop members.

It can especially be provided that the stop members limit the pivoting motion such that upon interaction thereof the sealing surface formed by the at least one electrode of the first jaw member is orientated in parallel to the longitudinal direction defined by the jaw member support.

A structurally simple configuration may provide that the stop members are designed as steps of the first jaw member or of the jaw member support adapted to be attached to each other.

The stop members preferably constitute guide members for guiding the first jaw member during pivoting relative to the jaw member support. In this way the jaw member can be pivoted in a defined manner and the closing width of the jaw members can be additionally limited.

As an alternative or in addition, it may be provided that one stop member is in the form of an oblong hole and the stop member interacting therewith is in the form of a pin engaging in the oblong hole. Stop members of this type can form the afore-mentioned guide members, for example.

As an alternative or in addition, it may be provided that the at least one stop member forms an adjustable actuator which is adjustable relative to the first jaw member and relative to the jaw member support, respectively. This enables the closing width to be adjusted by manipulating the actuator, for instance ex-works or by the user.

It is favorable when the actuator is adjustable to be locked.

In an advantageous embodiment of the instrument the stop members can be provided to be arranged on a side of the first jaw member and of the jaw member support facing away from the second jaw member.

As an alternative or in addition, it may be provided that the stop members are arranged on a side of the first jaw member and of the jaw member support facing the second jaw member.

For achieving a structurally simple configuration it is favorable when the stop members are formed integrally with a support element for the at least one electrode of the first jaw member and integrally with the jaw member support, respectively.

An advantageous embodiment of the instrument according to the invention includes a shank at the distal end of which the jaw member assembly is disposed, wherein at least one jaw member can be pivoted relative to the shank. The shank is, for example, the afore-mentioned jaw member support relative to which the second jaw member can be pivoted. It can also be provided that both jaw members can be pivoted relative to the shank.

In a different advantageous embodiment it is favorable when the instrument comprises two jaw member supports pivotal relative to each other, with one of the two jaw members being arranged at a respective distal end of each jaw member support. In this embodiment the jaw member supports form branches, for instance, that are pivotal about a pivot axis orientated transversely to the proximal-distal direction.

Thus the foregoing description especially comprises the embodiments of an electrosurgical instrument defined hereinafter in the form of consecutively numbered sentences:

1. An electrosurgical instrument having a proximal end and a distal end comprising:
    a jaw member assembly at the distal end including a first jaw member and a second jaw member movable relative thereto, wherein the jaw members can be transferred relative to each other from an opening position into a gripping position in which gripping position they are arranged to be closer to each other than in the opening position, each jaw member having at least one electrode connectable to an electric power source and electrodes of both jaw members being adapted to interact for sealing body tissue held between the jaw members in the gripping position;
    actuating means for transferring the jaw members from the opening position into the gripping position; and
    means for limiting the closing width of the jaw members when they are transferred from the opening position into the gripping position,
    characterized in that the means includes a plurality of limiting elements at most two limiting elements of which are arranged at one jaw member which limiting elements are in the form of an electrically insulating spacer projecting from the jaw member in the direction of the other jaw member over a sealing surface formed by the at least one electrode of the jaw member, wherein at least one spacer thereof being arranged at a distal end portion of the jaw member assembly.
2. The instrument according to sentence 1, characterized in that a total of only two limiting elements in the form of spacers are provided.
3. The instrument according to sentence 2, characterized in that the two spacers are arranged at different jaw members.
4. The instrument according to sentence 2, characterized in that the two spacers are arranged at the same jaw member.
5. The instrument according to any one of the preceding sentences, characterized in that at each jaw member at least one spacer is arranged.
6. The instrument according to any one of the preceding sentences, characterized in that two spacers arranged at a jaw member are disposed in the proximal-distal direction at the same or substantially at the same position.
7. The instrument according to sentence 6, characterized in that the two spacers are arranged transversely to the proximal-distal direction laterally adjacent each other at the jaw member.
8. The instrument according to any one of the preceding sentences, characterized in that at the distal end portion of the jaw member assembly exactly one spacer is arranged.
9. The instrument according to sentence 8, characterized in that the spacer is arranged in the center of the distal end portion.
10. The instrument according to any one of the preceding sentences, characterized in that at least one spacer is arranged proximally relative to the distal end portion, especially at a proximal end portion of the jaw member.
11. The instrument according to any one of the preceding sentences, characterized in that at least one spacer is integrated in the at least one electrode of the jaw member at which it is disposed.
12. The instrument according to sentence 11, characterized in that all spacers are integrated in the at least one electrode of the jaw member to which they are fixed.
13. The instrument according to any one of the preceding sentences, characterized in that at least one spacer is formed integrally with a support element of the jaw member at which it is disposed for the at least one electrode of said jaw member.
14. The instrument according to sentence 13, characterized in that all spacers are formed integrally with a support element of the respective jaw member at which they are arranged for the at least one electrode of said jaw member.
15. The instrument according to any one of the preceding sentences, characterized in that the instrument comprises a cutting means for severing body tissue held between the jaw members in the gripping position thereof, wherein the cutting means includes a cutting element that is or can be arranged transversely to the proximal-distal direction between two sealing surface portions of the respective at least one electrode of the jaw members.
16. The instrument according to sentence 15, characterized in that the cutting element is held at one of the jaw members.
17. The instrument according to sentence 15, characterized in that the cutting means comprises an actuating element for moving the cutting element in the proximal-distal direction and for transferring the latter from a retracted position into an advanced position, wherein during transfer body tissue held between the jaw members in the gripping position thereof is severed.
18. The instrument according to any one of the sentences 15 to 17, characterized in that at least one jaw member includes two separate electrodes each of which forms a sealing surface portion.
19. The instrument according to any one of the sentences 15 to 18, characterized in that at least one jaw member includes an electrode forming both sealing surface portions.
20. The instrument according to any one of the sentences 15 to 19, characterized in that transversely to the proximal-distal direction at least one spacer is arranged on each side of the cutting element.
21. The instrument according to sentence 20, characterized in that exactly one spacer is arranged on each side of the cutting element.

22. The instrument according to any one of the preceding sentences, characterized in that the means for limiting the closing width comprises at least one further limiting element not configured as a spacer which is arranged proximally with respect to the at least one spacer disposed at the distal end portion of the jaw member assembly.

23. The instrument according to any one of the preceding sentences, characterized in that the instrument includes a jaw member support for the first jaw member relative to which the second jaw member can be pivoted for transferring the jaw members from the opening position into the gripping position, and in that the first jaw member can be pivoted relative to the jaw member support about a pivot axis orientated transversely to a longitudinal direction defined by the jaw member support.

24. The instrument according to sentence 23, characterized in that the means for limiting the closing width comprises at least one further limiting element configured as a first stop member that is disposed at the first jaw member as well as at least one further limiting element configured as a second stop member that is disposed at the jaw member support and interacts for limiting the pivoting motion of the first jaw member relative to the jaw member support such that the proximal end of the first jaw member is pivoted toward the second jaw member.

25. The instrument according to sentence 24, characterized in that the stop members limit the pivoting motion so that upon interaction thereof the sealing surface formed by the at least one electrode of the first jaw member is orientated in parallel to the longitudinal direction defined by the jaw member support.

26. The instrument according to sentence 24 or 25, characterized in that the stop members are in the form of steps of the first jaw member and of the first jaw member support, resp., adapted to be attached to each other.

27. The instrument according to any one of the sentences 24 to 26, characterized in that the stop members constitute guide members for guiding the first jaw member during pivoting relative to the jaw member support.

28. The instrument according to any one of the sentences 24 to 27, characterized in that a stop member is formed as oblong hole and the stop member interacting therewith is formed as pin engaging in said oblong hole.

29. The instrument according to any one of the sentences 24 to 28, characterized in that at least one stop member forms an adjustable actuator that is adjustable relative to the first jaw member and relative to the jaw member support, respectively.

30. The instrument according to sentence 29, characterized in that the actuator is adjustable to be locked.

31. The instrument according to any one of the sentences 24 to 30, characterized in that the stop members are arranged on a side of the first jaw member and of the jaw member support facing away from the second jaw member.

32. The instrument according to any one of the sentences 24 to 31, characterized in that the stop members are arranged on a side of the first jaw member and of the jaw member support facing the second jaw member.

33. The instrument according to any one of the sentences 24 to 32, characterized in that the stop members are formed integrally with a support element for the at least one electrode of the first jaw member and integrally with the jaw member support, respectively.

34. The instrument according to any one of the preceding sentences, characterized in that the instrument includes a shank at the distal end of which the jaw member assembly is disposed, wherein at least one jaw member can be pivoted relative to the shank.

35. The instrument according to any one of the sentences 1 to 33, characterized in that the instrument comprises two jaw member supports pivotal relative to each other, wherein one of the two jaw members is disposed at a respective distal end of each jaw member support.

BRIEF DESCRIPTION OF THE DRAWING FIGURES

Figure 2:
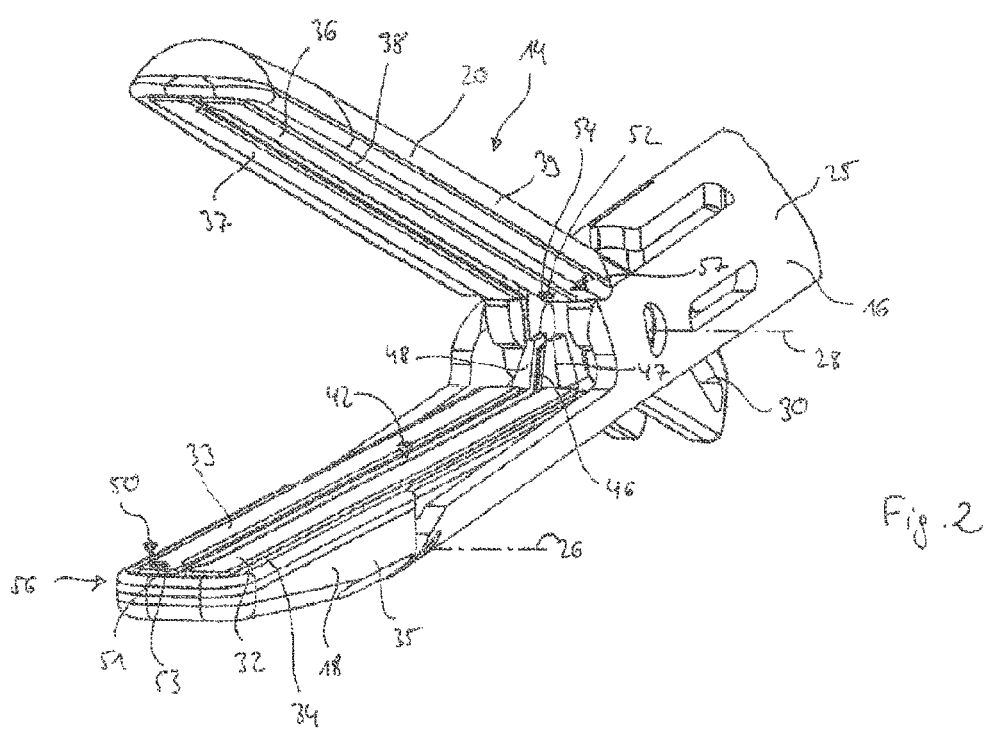
Figure 3:
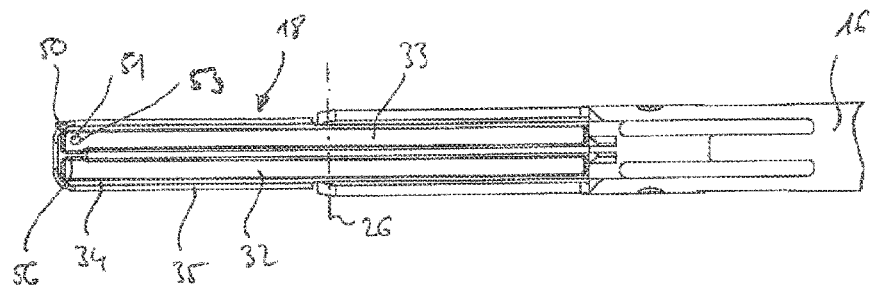
Figure 4:
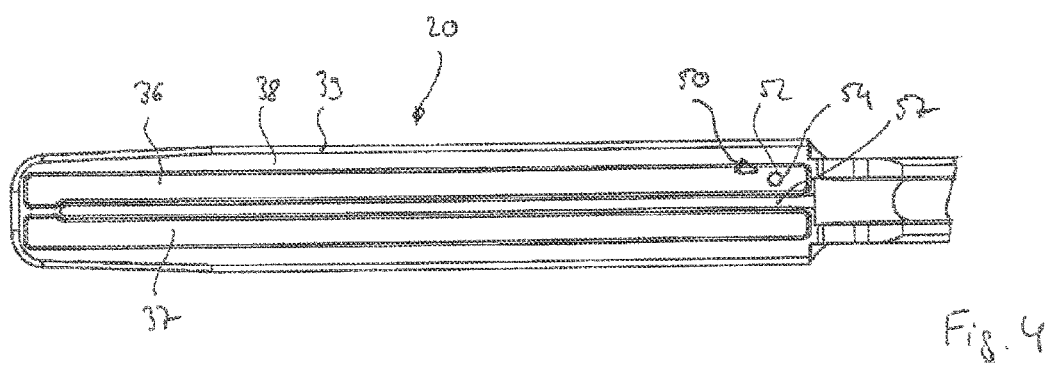
Figure 6A:
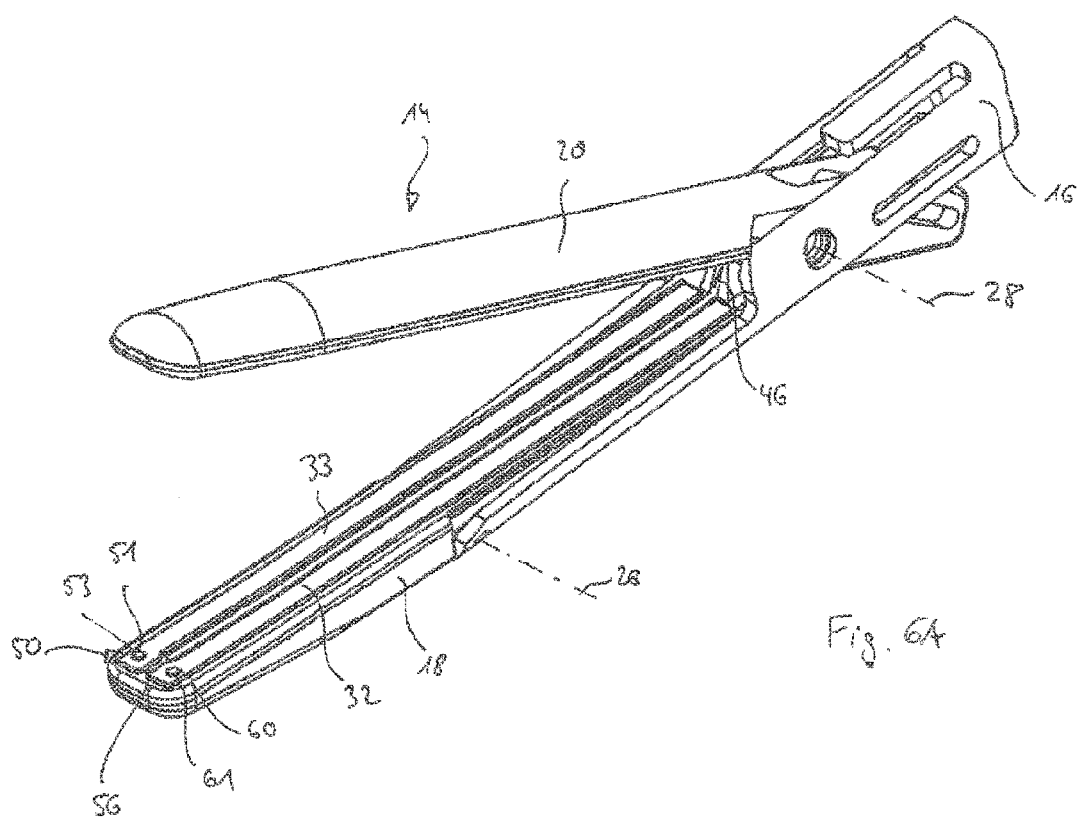
Figure 6B:
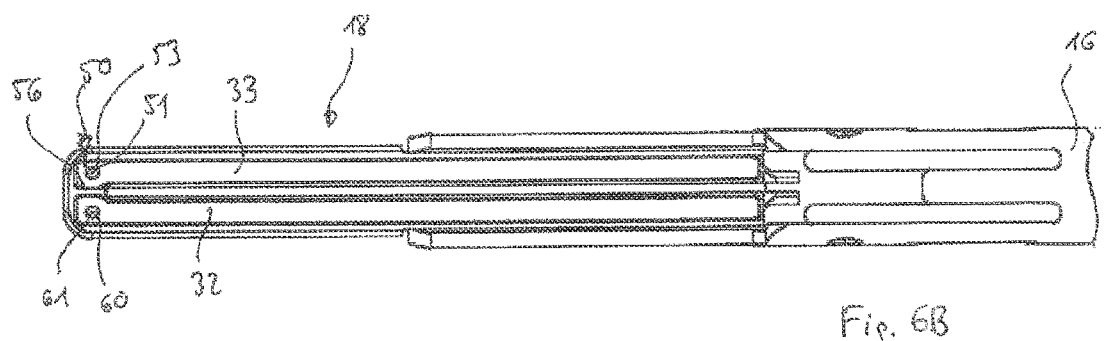
Figure 7A:
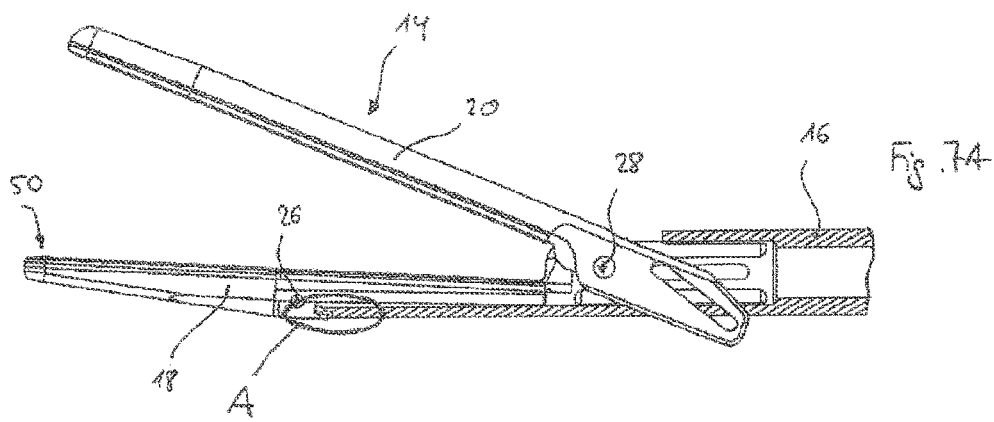
Figure 7B:
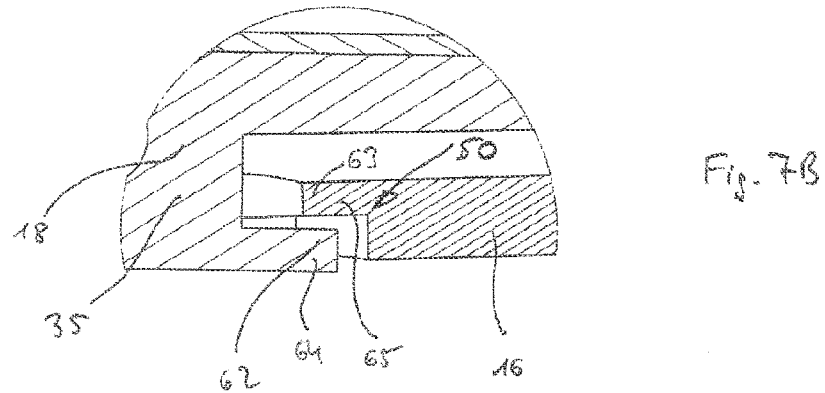
Figure 8A:
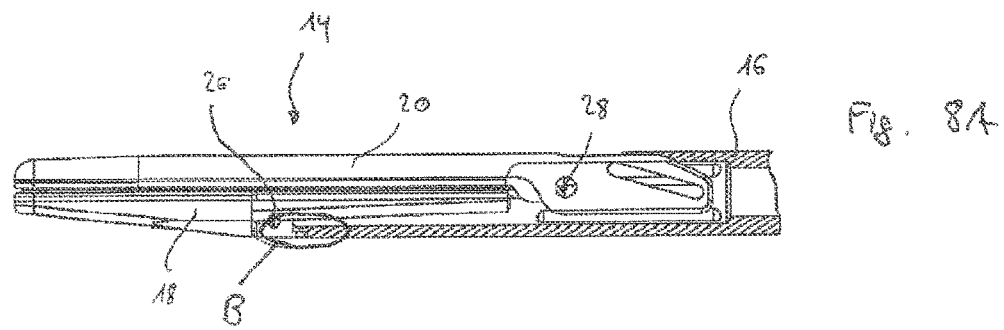
Figure 8B:
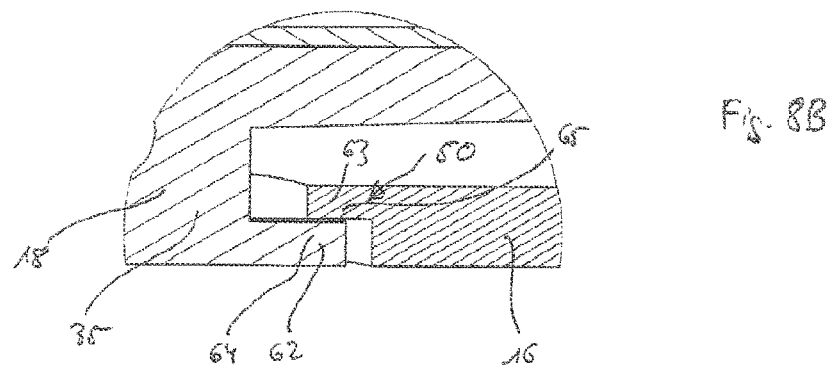
Figure 9A:
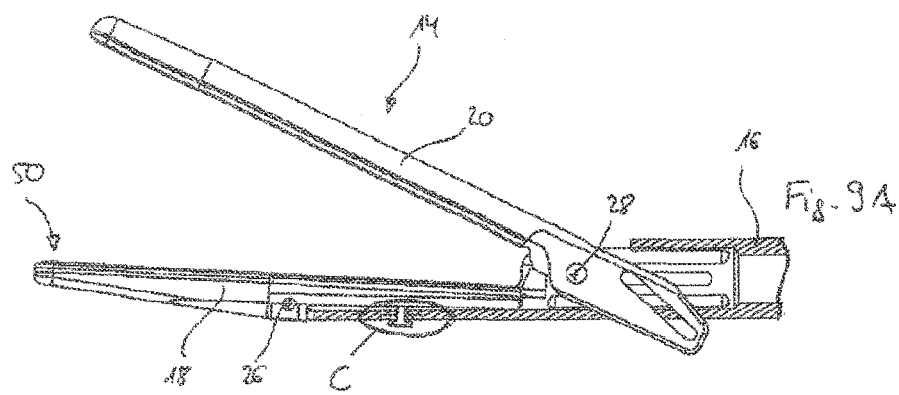
Figure 9B:
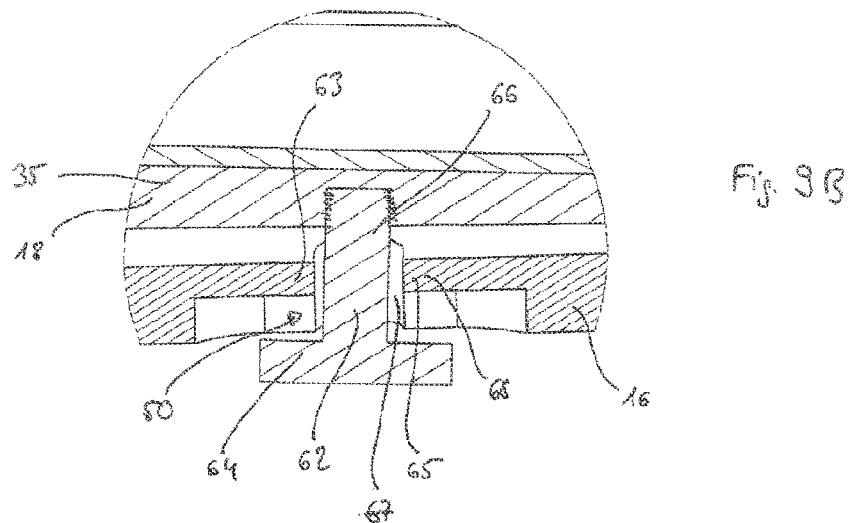
Figure 10A:
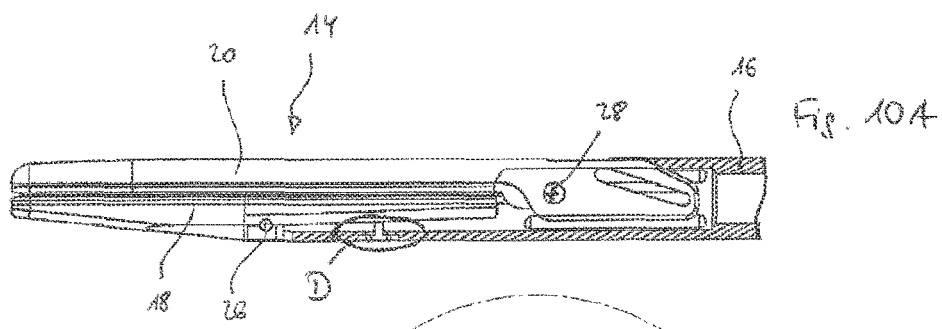
Figure 10B:
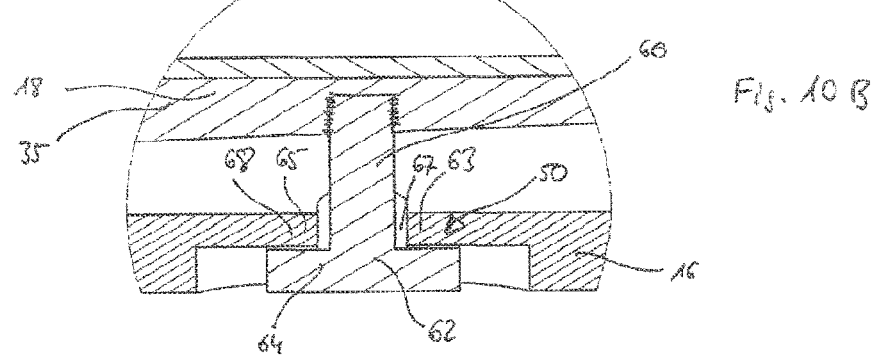
Figure 11A:
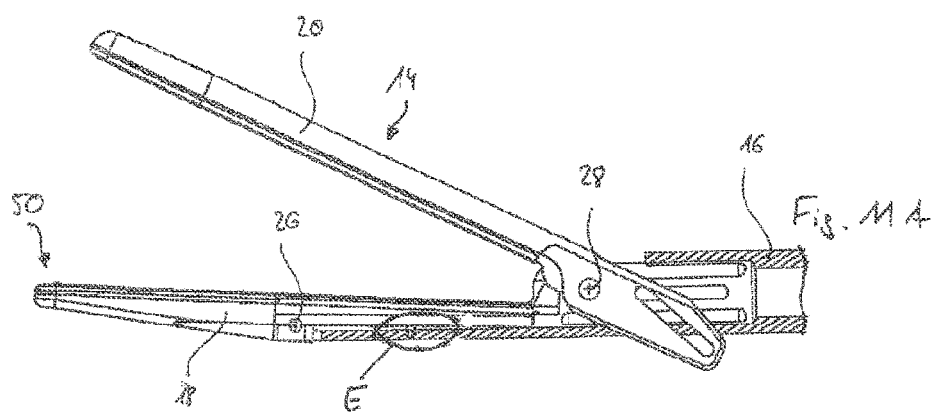
Figure 11B:
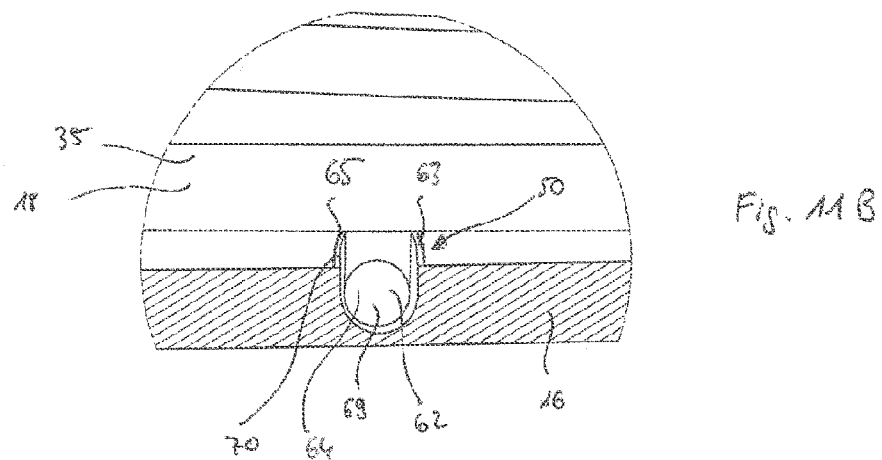
Figure 12A:
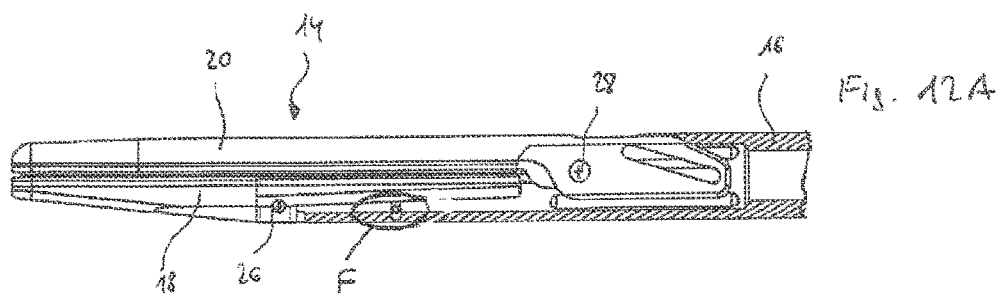
Figure 12B:
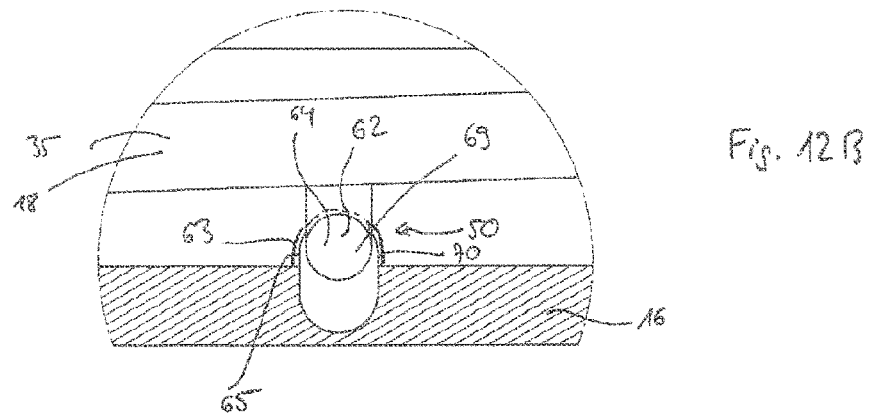
Figure 13A:
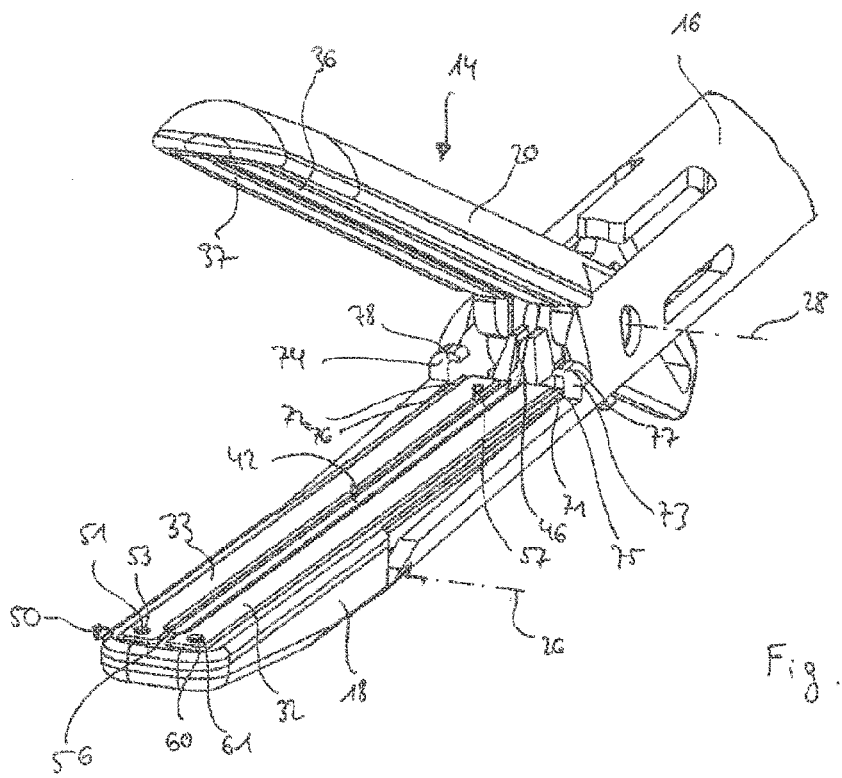
Figure 13B:
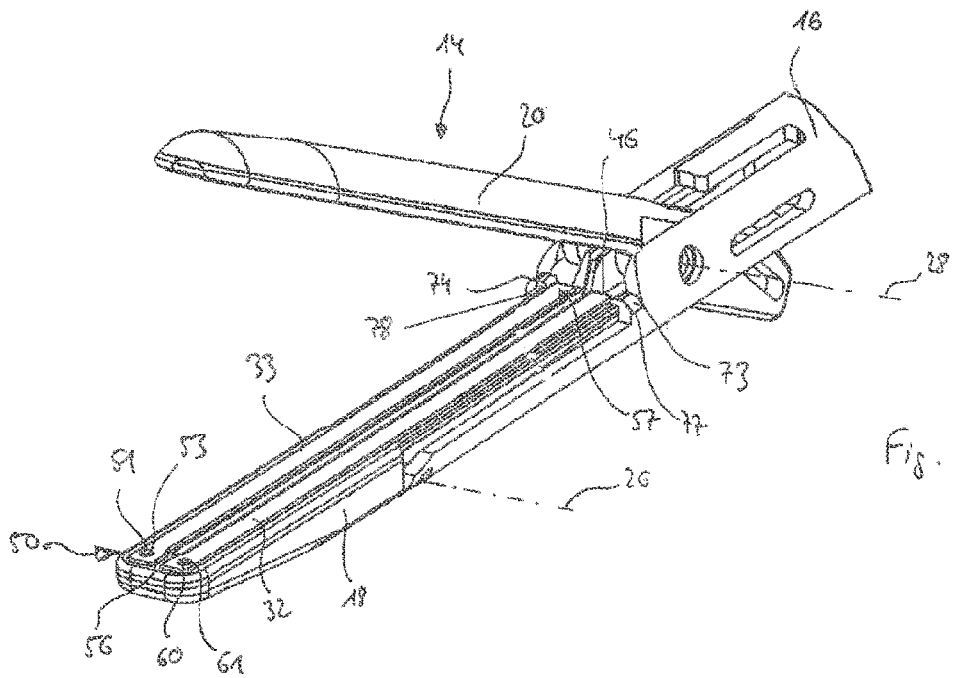
Figure 14:
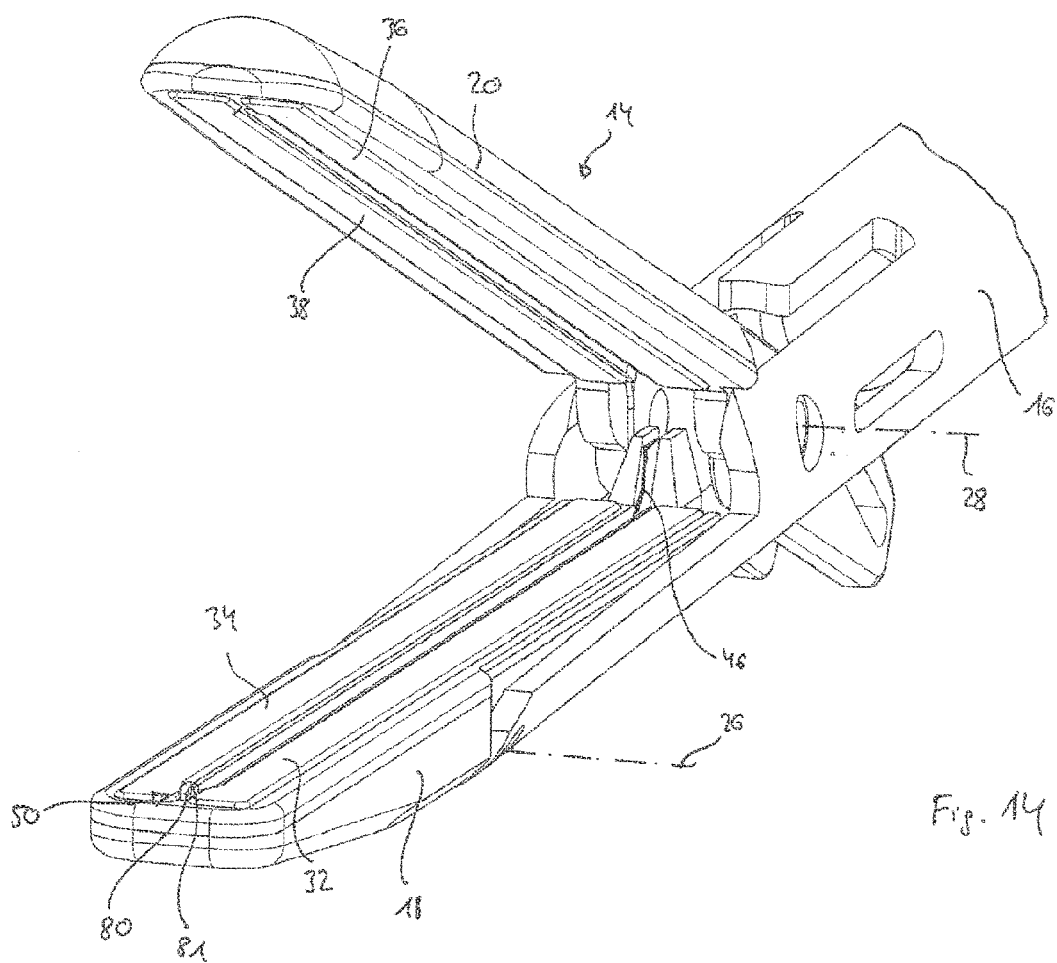
Figure 15:
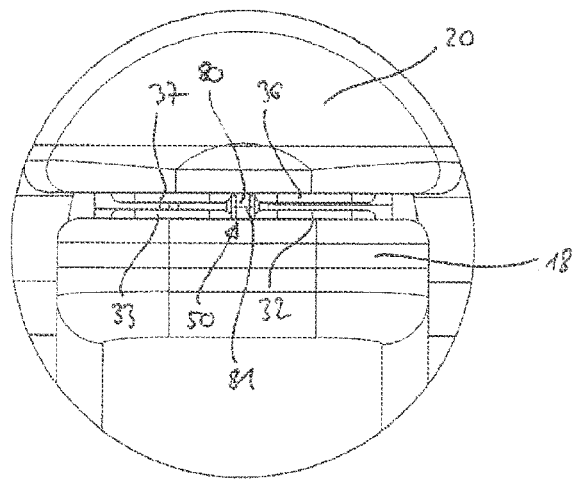

The following description of preferred embodiments of the invention serves for a detailed illustration of the invention in connection with the drawing, in which:

FIG. 1: is a perspective view of a first preferred embodiment of an electrosurgical instrument according to the invention including a shank and at the distal end thereof a jaw member assembly having two jaw members movable relative to each other, the jaw members being shown in an opening position;

FIG. 2: is an enlarged view of detail "2" in FIG. 1;

FIG. 3: is a top view onto a distal end of the shank and a first jaw member of the instrument of FIG. 1;

FIG. 4: is a top view onto the other jaw member of the instrument of FIG. 1;

FIG. 5: is an end-side view of the instrument of FIG. 1 in the distal-proximal direction, the jaw members adopting a gripping position;

FIG. 6A: is a view corresponding to FIG. 2 in a second preferred embodiment of the instrument according to the invention;

FIG. 6B: is a top view onto a distal end of the shank and a jaw member of the second preferred embodiment of the instrument;

FIG. 7A: is a side view of the distal end of the shank and the jaw member assembly of FIG. 6, which is partly cut, with the jaw members adopting the opening position;

FIG. 7B: is a representation of detail A in FIG. 7A;

FIG. 8A: is a representation corresponding to FIG. 7A, with the jaw members adopting the gripping position;

FIG. 8B: is a representation of detail B in FIG. 8A;

FIG. 9A: is a representation corresponding to FIG. 7A in a third preferred embodiment of the instrument according to the invention, with the jaw members adopting an opening position;

FIG. 9B: is a representation of detail C in FIG. 9A;

FIG. 10A: is a representation corresponding to FIG. 9A, with the jaw members adopting a gripping position;

FIG. 10B: is a representation of detail D in FIG. 10A;

FIG. 11A: is a representation corresponding to FIG. 7A in a fourth preferred embodiment of the instrument according to the invention, with the jaw members adopting an opening position;

FIG. 11B: is a representation of detail E in FIG. 11A;

FIG. 12A: is a representation corresponding to FIG. 11A, with the jaw members adopting the gripping position;

FIG. 12B: is a representation of detail F in FIG. 12A;

FIG. 13A: is a representation corresponding to FIG. 2 in a fifth preferred embodiment of the instrument according to the invention, with the jaw members adopting an opening position and a first jaw member being spaced apart from stop members disposed at the shank;

FIG. 13B: is a representation corresponding to FIG. 13, the first jaw member abutting against the stop members at the shank;

FIG. 14: is a view corresponding to FIG. 2 in a sixth preferred embodiment of the instrument according to the invention, with the jaw members adopting an opening position;

FIG. 15: is an end-side view of the instrument of the sixth embodiment in the distal-proximal direction, with the jaw members adopting a gripping position;

FIG. 16: is a representation corresponding to FIG. 2 in a seventh preferred embodiment of the instrument according to the invention, with the jaw members adopting an opening position;

FIG. 17A: is a side view of the embodiment according to FIG. 16, with the jaw members adopting a gripping position;

FIG. 17B: is an enlarged representation of detail G in FIG. 17A and

FIG. 18: is a perspective representation of an eighth preferred embodiment of an instrument according to the invention.

DETAILED DESCRIPTION

FIG. 1 shows, in perspective representation, a first preferred embodiment provided with reference numeral 10 of an instrument for sealing and cutting body tissue according to the invention. The instrument 10 is in the form of a bipolar tubular shaft instrument having a handle 12 at a proximal end and a jaw member assembly 14 at a distal end.

In the present case "proximal" and "distal" are to be understood as related to a user handling the instrument 10. The user handles the instrument 10 at the proximal end by the handle 12 and acts on body tissue by the distal end including the jaw member assembly 14.

The jaw member assembly 14 is held at a straight shank 16 anchored in the handle 12. A mechanism known per se is arranged in the handle 12 and in the shank 16 so as to move two jaw members 18 and 20 of the jaw member assembly 14 relative to each other. For this purpose, the instrument 10 further includes an actuating means 22 which at the handle 12 comprises an actuating lever 24 operable by the user. By pulling at the actuating lever 24 the jaw members 18 and 20 can be transferred in a way known per se from an opening position shown in FIGS. 1 and 2 into a gripping position.

In the opening position the jaw members 18 and 20 are spaced apart relative to each other, which in the present case is also understood to be a spread position of the jaw members 18 and 20 shown in FIGS. 1 and 2. The gripping position of the jaw members 18 and 20 is only shown in the end-side view of FIG. 5. In a side view the jaw members 18 and 20 in the gripping position adopt a position relative to each other, as it is illustrated for the case of further advantageous embodiments of the instrument in FIGS. 8A, 10A, 12A and 17A. In the gripping position the jaw members 18 and 20 are spaced apart from each other less than in the opening position, which will be discussed hereinafter.

The shank 16 constitutes a jaw member support 25 at the distal end of which the first jaw member 18 is pivotally supported about a pivot axis 26 orientated transversely to the longitudinal direction defined by the shank 16. The first jaw member 18 can pivot relative to the shank 16 about a comparatively small angular range and its distal end is biased in the direction of the second jaw member 20 by a biasing means not shown in the drawing, for example a spring element.

The second jaw member 20 is pivotally supported on the shank 16 proximally with respect to the first jaw member 18 about a pivot axis 28 orientated transversely to the longitudinal direction of the shaft 16. A pulling member guided in the shank 16 in the proximal-distal direction and not shown in the drawing can engage in a control gate 30 of the second jaw member 20 so that the latter is transferred, as afore-mentioned, from the opening position into the gripping position by acting on the actuating lever 24. In so doing, the jaw member 20 pivots about the pivot axis 28 in the direction of the jaw member 18.

For sealing body tissue the jaw member 18 comprises two electrodes 32 and 33 extending in the proximal-distal direction and being spaced apart from each other transversely to the proximal-distal direction. Each of the electrodes 32 and 33 is held in an electrically insulating support element 34 of the jaw member 18 which in turn is disposed in a mount 35 by means of which the jaw member 18 is fixed to the shank 16.

In a similar way, the jaw member 20 has two electrodes 36 and 37 extending in the proximal-distal extension and being spaced apart from each other transversely to the longitudinal direction of the shank which in turn are mounted in an electrically insulating support element 38. The support element in turn is arranged in a mount 39 by means of which the jaw member 20 is fixed to the shank 16.

The electrodes 32, 33, 36 and 37 are communicated via a connecting cable 40 of the instrument 10 with an electrosurgical bipolar high-frequency generator not shown in the drawing and can be energized by the same. For this purpose, a user can actuate an actuating member 41 at the handle 12.

The electrodes 32 and 33 are usually located on the same potential, just as the electrodes 36 and 37 the potential of which differs from that of the electrodes 32 and 33. In the gripping position of the jaw members 18 and 20 body tissue caught between the same can be sealed by electrosurgery in that current flows between the electrodes 32 and 36 as well as between the electrodes 33 and 37.

Instead of two electrodes for each jaw member, also only one electrode could be provided for each jaw member or else a larger number of electrodes could be provided for each jaw member.

As afore-mentioned, the electrodes 32 and 33 as well as 36 and 37 are spaced apart from each other transversely to the longitudinal direction of the instrument 10. Furthermore, the support elements 34 and 38 include central recesses so that a proximal-distal passage 42 is formed between the electrodes 32 and 33 as well as 36 and 37.

The instrument 10 comprises a cutting means 44 including an actuating member 45 disposed at the handle 12 as well as a cutting element 46 which can be acted upon by the actuating member 45. The cutting element 46 is supported at the shank 16 to be movable in the proximal-distal direction and can be transferred from a retracted position (FIG. 2) into an advanced position not shown in the drawing.

In the retracted position the cutting element 46 is arranged between truncated pyramidal projections 47 and 48 of the support element 34 at the proximal end thereof. From the retracted position the cutting element 46 can be shifted into the advanced position only after transferring the jaw members 18 and 20 into the gripping position, wherein it is moved in the passage 42. This permits severing body tissue caught by the jaw members 18 and 20 and sealed by the electrodes 32, 33, 36 and 37 by means of the cutting element 46.

In order to achieve a reliable sealing of body tissue the instrument 10 includes a means for limiting the closing width of the jaw members 18 and 20, hereinafter simply abbreviated to "means" 50. The means 50 serves for limiting the closing width of the jaw members 18 and 20 relative to each other when they are transferred into the gripping position. In this way electric short-circuit between the electrodes 32 and 36 as well as 33 and 37 can be largely prevented. The body tissue to be sealed can thus be manipulated in a more controllable manner and can be more reliably sealed.

The means 50 comprises two limiting elements 51 and 52 in the form of spacers 53 and 54, resp. The spacers 53 and 54 are electrically insulating. The spacer 53 is integrated in the electrode 33, namely at a distal end portion 56 of the jaw member assembly 14. For example, the spacer 53 is arranged in a recess in the electrode. It is also imaginable that the spacer 53 is formed integrally with the support element 34 and passes through the electrode 33.

The spacer 54 is arranged at a proximal end portion 57 of the jaw member assembly 14 and is integrated in the electrode 36. Thus the means 50 comprises two spacers 53, 54 disposed on opposite sides of the passage 42 and of the cutting element 46 to be arranged thereto, at least one of which is arranged in the distal end portion 56.

The spacers 53, 54 project from the electrosurgical sealing surfaces formed by the electrodes 32 and 33, on the one hand, and 36 and 37, resp., in the direction of the respective other jaw member 20 and 18, resp. For example, the spacers 53 and 54 project from the electrodes 32, 33 and 36, 37, resp., by approx. 25 µm to approx. 250 µm, more preferably by approx. 100 µm to approx. 200 µm.

As afore-mentioned, by the means 50 and thus by the spacers 53 and 54 short-circuit of the electrodes 32 and 36 as well as 33 and 37 can be largely prevented. When the jaw members 18 and 20 are transferred into the gripping position so as to catch body tissue between them, the spacer 53 contacts the electrode 37 and the spacer 54 contacts the electrode 32 (FIG. 5). In so doing, first the electrode 37 is contacted by the spacer 53, because the jaw member 18 is biased distally in the direction of the jaw member 20.

As a result, by means of the instrument 10 an improved sealing effect can be achieved in that short-circuit between the electrodes of the jaw members 18 and 20 can be prevented even when body tissue to be sealed has dimensions that are definitely smaller than those of the electrodes 32, 33, 36 and 37. The jaw members 18 and 20 are supported relative to each other both distally and proximally and further on both sides of the passage 42 by means of the spacers 53 and 54. When transferring the jaw members 18 and 20 into the gripping position, thus furthermore deformations and warping of the electrodes 32, 33, 36 and 37 as well as of the support elements 34 and 38 thereof can be largely prevented.

Moreover, it is of advantage that a total of only two spacers 53 and 54 are used so that the sealing surfaces of the electrodes 32, 33, 36 and 37 are largely maintained. In the area of the merely point-shaped spacers 53 and 54 the heat formed in the current flow can expand so that even tissue areas that contact the insulating spacers 53 and 54 can be sealed.

Instead of the point-shaped spacers 53 and 54 shown here, also spacers of different shape, for example strip-shaped, rectangular or triangular spacers can be provided. The spacer 53 could also be integrated in one of the electrodes 32, 36 and 37 and the spacer 54 could be integrated in one of the electrodes 32, 33 and 37.

Hereinafter a preferred second embodiment of the instrument according to the invention illustrated only in sections in the FIGS. 6A to 8B is referred to, which is not shown in the drawing itself but is configured just like the instrument 10, however, apart from the differences described in the following. This applies mutatis mutandis to the further advantageous embodiments of the instrument according to the invention illustrated hereinafter as well.

The above-explained advantages achievable by the instrument 10 can be equally achieved by the now explained further embodiments. For equal and equally acting components and features identical reference numerals are used.

In the second embodiment of the invention according to FIGS. 6A to 8B the means 50 comprises a limiting element 60 in the form of a spacer 61 instead of the spacer 54. The spacer 61 is integrated in the electrode 32, viz. laterally next to the spacer 53 related to a direction transverse to the longitudinal direction of the instrument 10. Thus in the second embodiment the jaw member 18 includes two spacers 53 and 61 at the distal end portion 56. During transfer of the jaw members 18 and 20 short-circuit between the electrodes 32 and 36 as well as 33 and 37 can be prevented especially efficiently at the distal end portion 56.

Other than shown in FIGS. 6A and 6B, the spacers 53 and 61 could also be arranged at the electrodes 36 and 37.

For limiting the closing width on the proximal side, in the second embodiment the means 50 comprises two further limiting elements 62 and 63 in the form of stop members 64 and 65, respectively. The stop members 64 and 65 are arranged virtually on the proximal side of the pivot axis 26 on the side of the jaw member 18 and the shank 16 facing away from the jaw member 20 and are designed as respective steps attachable to each other. The stop member 64 is formed integrally with the mount 35 of the jaw member 18 and the stop member 65 is formed integrally with the distal end of the shank 16.

When the jaw members 18 and 20 adopt the opening position, the stop members 64 and 65 are spaced apart from each other (FIGS. 7A and 7B). When the jaw members 18 and 20 are transferred into the gripping position, the spacers 53 and 61 first contact the electrodes 37 and 36, respectively, as the jaw member 18 is biased distally with respect to the jaw member 20. This results in pivoting the jaw member 18 about the pivot axis 26, wherein the proximal end of the jaw member 18 is pivoted toward the proximal end of the jaw member 20. The pivoting motion is limited by the stop members 64 and 65 which get into contact with each other (FIG. 8B). This results in the fact that the closing width of the jaw members 18 and 20 is limited on the proximal side by the stop members 64 and 65. In the second embodiment according to FIGS. 6A to 8B therefore no proximal spacer needs to be provided, which nevertheless could be present, as a matter of course.

In a third embodiment of the invention shown in sections in FIGS. 9A to 10B the limiting elements 62 and 63 of the means 50 are equally provided in the form of the stop members 64 and 65. The stop member 64 in the third embodiment is configured as adjustable actuator adapted to be fixed to the support element 34 in the form of a screw 66. The screw 66 passes through a breakthrough 67 at the distal end of the shank 16 the rim 68 of which forms the stop member 65.

By means of the screw 66 the closing width of the jaw members 18 and 20 can be adjusted either by the manufacturer or by the user depending on how far the screw 66 is screwed into the support element 34.

In the opening position of the jaw members 18 and 20 a head of the screw 66 has a distance from the rim 68. The pivoting of the jaw member 18 about the pivot axis 26 and thus the closing width of the jaw members 18 and 20 on the proximal side is limited by the fact that the head of the screw 66 abuts against the rim 68 when the jaw members 18 and 20 are transferred into the gripping position (FIG. 10B).

In a fourth embodiment of the invention partly shown in FIGS. 11A to 12B the limiting elements 62 and 63 are equally provided in the form of the stop members 64 and 65. The stop member 64 is in the form of a pin 69 fixed at the support element 34. The pin 69 engages in the stop member 65 in the form of an oblong hole 70 fixed at the distal end of the shank 16.

When the jaw members 18 and 20 of the fourth embodiment are transferred from the opening position (FIGS. 11A and 11B) into the gripping position, the pin 69 can move in the oblong hole 70 until it abuts against the end face thereof (FIG. 12B). This limits the pivoting motion of the jaw member 18 about the pivot axis 26 and thus the closing width of the jaw members 18 and 20 on the proximal side. Moreover the pin 69 and the oblong hole 70 constitute guide members for guiding the pivoting of the jaw member 18 about the pivot axis 26.

In a fifth embodiment of the invention partly illustrated in FIGS. 13A and 13B, limiting elements 71 to 74 of the means 50 are provided that are disposed on the respective side of the jaw member 18 and of the shank 16 facing the jaw member 20. The limiting elements 71 to 74 are stop members 75 to 78 the stop members 75 and 76 of which are formed by the proximal end of the support element 34. The stop members 75 and 76 are disposed at an outer rim laterally adjacent to the electrodes 32 and 33, respectively.

The stop members 77 and 78 are arranged at the shank 16 somewhat distally from the pivot axis 28, have a hook shape and encompass the support element 34. When the jaw members 18 and 20 of the fifth embodiment adopt the opening position, the stop members 75 and 77 are spaced apart from each other just as the stop members 76 and 78 (FIG. 13A). When the jaw members 18 and 20 are transferred into the gripping position, the jaw member 18 is thus pivoted about the pivot axis 26. The stop members 75 and 77 as well as 76 and 78 can get into contact with each other so as to limit pivoting of the jaw member 18. This is illustrated in FIG. 13B, wherein for better visibility only the jaw members 18 and 20 do not adopt the gripping position but the opening position. In this way the stop members 75 to 78 serve for proximal-side limitation of the closing width of the jaw members 18 and 20.

Limiting elements and stop members as described in the foregoing with reference to FIGS. 7A to 13B could also be provided in the first embodiment of the invention according to FIGS. 1 to 5.

Moreover, limiting elements and stop members as described with reference to FIGS. 7A to 13B are present in the sixth embodiment of the invention discussed hereinafter and partly illustrated in FIGS. 14 and 15 for limiting the closing width of the jaw members 18 and 20 there.

In the sixth embodiment the means 50 comprises at the distal end portion 56 only one single limiting element 80 in the form of a spacer 81. The spacer 81 is disposed on the distal side of the passage 42 between the distal ends of the electrodes 32 and 33 and is formed integrally with the support element 34. Compared to this, in the sixth embodiment no spacer is integrated in one of the electrodes 32, 33, 36 and 37. This could be equally provided, as a matter of course.

The spacer 81 is dimensioned so that in the gripping position of the jaw members 18 and 20 (FIG. 15) the electrodes 32 and 36 as well as 33 and 37 still have a distance from each other which approximately corresponds to the distance to be obtained by the spacers 53 and 54.

Apart from the spacer 81, further spacers that are formed integrally with the support element 34 and the support element 38, resp., could be provided at the jaw member 18 or at the jaw member 20.

Instead of the nipple shape shown in FIGS. 14 and 15, the spacer 81 could also have a different shape and could exhibit, for example, a cylindrical, rib, tapered or truncated, pyramidal or truncated pyramidal shape. The spacer 81 could also be arranged distally from the electrodes 32 and 33.

A seventh embodiment of the invention shown in FIGS. 16 and 17A differs from the afore-explained sixth embodiment according to FIGS. 14 and 15 by the fact that in the seventh embodiment the closing width of the jaw members 18 and 20 can be limited on the proximal side by a limiting element 83 of the means 50. The limiting element 83 is configured as spacer 84 disposed on the proximal side of the electrode 36 and formed integrally with the support element 38. The spacer 84 exhibits a strip shape and projects from the support element 38 in the direction of the jaw member 18 just as far as the spacer member 81 projects from the support element 34 in the direction of the jaw member 20.

When the jaw members 18 and 20 of the seventh embodiment adopt the opening position, the spacer 84 is spaced relative to the support element 34 (FIG. 16). When the jaw members 18 and 20 adopt the gripping position, the spacer 84 can be adjacent to the proximal end of the support element 34 and thus limit the closing width of the jaw members 18 and 20 on the proximal side (FIGS. 17A and 17B).

Accordingly, on the proximal side of the electrode 33 or of the electrode 37 another proximal spacer could be provided in the seventh embodiment. Equally the spacer 84 could be provided in the further embodiments of the invention explained here.

The foregoing description illustrates that all embodiments of the invention comprise at least one spacer disposed at the distal end portion 56 of the jaw member assembly 14 for limiting the closing width of the jaw members 18 and 20 on the distal side. In addition, a maximum of two spacers are provided for each jaw member 18 or 20. In the gripping position the jaw members 18 and 20 therefore can rest on each other in order to prevent electric short-circuits. At the same time a good sealing result can be achieved, as the sealing effect of the electrodes 32, 33, 36 and 37 is not impaired by the small dimensions and the small number of spacers.

FIG. 18 in a perspective view illustrates an eighth preferred embodiment of an instrument according to the invention denoted with the reference numeral 90. The instrument 90 likewise is a bipolar electrosurgical instrument and the advantages to be achieved by the instrument 10 can also be achieved by the instrument 90. The foregoing remarks are referred to in this respect.

The instrument 90 includes a handle 91 comprising two handle elements 93 and 94 adapted to be pivoted relative to each other about a pivot axis 92. Each of the handle elements 93, 94 constitutes a jaw member support 95 and 96, respectively. At the jaw member support 95 a jaw member 97 is distally fixed and at the jaw member support 96 a jaw member 98 is distally fixed.

The jaw members 97 and 98 can exhibit all features and components which were illustrated in the foregoing by the example of the jaw members 18 and 20, respectively. For instance, the jaw member 97 can correspond to the jaw member 18 and the jaw member 98 can correspond to the jaw member 20, or vice versa. This applies mutatis mutandis to the jaw member supports 95 and 96 in respect of the jaw member support 25. When the handle elements 93 and 94 are pivoted relative to each other about the pivot axis 92, the jaw members 97 and 98 can be transferred from an opening position into a gripping position so as to grip body tissue to be sealed.

The instrument 90, too, includes a cutting means 99 having an actuating member 100 disposed at the handle 91. A cutting element not shown in the drawing can thus be shifted in the proximal-distal direction so as to sever body tissue caught between the jaw members 97 and 98.

The invention claimed is:

1. An electrosurgical instrument having a proximal end and a distal end comprising:
    a jaw member assembly at the distal end including a first jaw member and a second jaw member movable relative thereto, wherein the first and second jaw members can be moved relative to each other from an open position into a gripping position in which the first and second jaw members are arranged to be closer to each other than in the open position, each of the first and second jaw members of the jaw member assembly having at least one electrode connectable to an electric power source and the at least one electrode of both of the first and second jaw members being adapted to interact for sealing body tissue held between the first and second jaw members in the gripping position;
    actuating means for transferring the first and second jaw members from the open position into the gripping position; and
    elements for limiting a closing width of the first and second jaw members when the first and second jaw members are moved from the open position into the gripping position,
wherein the elements for limiting the closing width of the first and second jaw members consist of two electrically insulating spacers, one of the two electrically insulating spacers located only at a distal end of the first jaw member and projecting from the first jaw member in a direction of the second jaw member over a sealing surface formed by the at least one electrode of the first jaw member, and another of the two electrically insulating spacers located only at a proximal end of the second jaw member and projecting from the second jaw member in a direction of the first jaw member over a sealing surface formed by the at least one electrode of the second jaw member.

2. The electrosurgical instrument according to claim 1, wherein at least one of the two electrically insulating spacers is formed integrally with a support element of the first jaw member on which the one of the two electrically insulating spacers is disposed.

3. The electrosurgical instrument according to claim 2, wherein another of the two electrically insulating spacers is formed integrally with a support element of the second jaw member on which the another of the electrically insulating spacers is disposed.

4. The electrosurgical instrument according to claim 1, wherein the electrosurgical instrument comprises a cutting means for severing the body tissue held between the first and second jaw members in the gripping position thereof, wherein the cutting means includes a cutting element that is or can be arranged between two sealing surface portions of the at least one electrode of the first and second jaw members.

5. The electrosurgical instrument according to claim 4, wherein the cutting means comprises an actuating element for moving the cutting element in the proximal-distal direction and for transferring the cutting element from a retracted position into an advanced position, wherein the body tissue held between the first and second jaw members in the gripping position thereof is configured to be severed during transferring of the cutting element into the advanced position.

6. The electrosurgical instrument according to claim 4, wherein the at least one electrode of the at least one jaw member of the first and second jaw members includes two separate electrodes, each of the two separate electrodes forming a sealing surface portion.

7. The electrosurgical instrument according to claim 4, wherein the one of the two electrically insulating spacers projecting from the first jaw member is arranged transversely to the proximal-distal direction on one side of the cutting element, and the another of the two electrically insulating spacers projecting from the second jaw member is arranged transversely to the proximal-distal direction on another side of the cutting element.

8. The electrosurgical instrument according to claim 1, wherein the electrosurgical instrument includes a jaw member support for the first jaw member relative to which the second jaw member can be pivoted for transferring the first and second jaw members from the open position into the gripping position, and in that the first jaw member can be pivoted relative to the jaw member support about a pivot axis orientated transversely to a longitudinal direction defined by the jaw member support.

* * * * *